United States Patent

Newman et al.

(10) Patent No.: US 10,260,414 B2
(45) Date of Patent: Apr. 16, 2019

(54) FOAM PLUG FOR ENGINE COVER FASTENER POCKET

(71) Applicant: Ford Global Technologies, LLC, Dearborn, MI (US)

(72) Inventors: Christopher William Newman, Farmington Hills, MI (US); Gary Nola, Saline, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 80 days.

(21) Appl. No.: 15/363,770

(22) Filed: Nov. 29, 2016

(65) Prior Publication Data

US 2018/0149081 A1 May 31, 2018

(51) Int. Cl.
*F02B 77/00* (2006.01)
*A61F 2/44* (2006.01)

(52) U.S. Cl.
CPC ............ *F02B 77/005* (2013.01); *A61F 2/446* (2013.01); *Y10T 428/24008* (2015.01)

(58) Field of Classification Search
CPC ............ Y10T 428/24008; F16B 37/14; B60R 13/0838; F02B 77/005
USPC .......................................................... 428/99
See application file for complete search history.

(56) References Cited

U.S. PATENT DOCUMENTS

| 4,394,096 | A | 7/1983 | Stevens |
| 5,827,029 | A | 10/1998 | Denman |
| 8,282,327 | B2 | 10/2012 | Miyagawa et al. |
| 8,870,508 | B2 | 10/2014 | Hsu |
| 2015/0345315 | A1 | 12/2015 | Orieux et al. |

FOREIGN PATENT DOCUMENTS

GB 2489472 10/2012

*Primary Examiner* — Alexander S Thomas
(74) *Attorney, Agent, or Firm* — LeClairRyan

(57) ABSTRACT

An engine cover assembly including a fastener concealing plug is disclosed. The plug includes a conical wall having upper and lower ends. A lower circumferential ring is spaced apart from the upper ring. The lower end of the concealing plug includes a fastener-receiving recessed area. The fastener pocket of the engine cover includes upper and lower grooves having a ring area formed therebetween. The upper circumferential ring of the plug nests with the upper groove of the pocket, the recessed area of the plug nests with the ring area, and the lower circumferential ring of the plug nests with the lower groove of the pocket. The engine cover is positioned on the engine such that a cover attaching stud passes through a stud-passing aperture of the cover. A fastening nut is threaded onto the cover-attaching stud until it comes into contact with a compression-limiting spacer. The plug conceals the fastener.

14 Claims, 5 Drawing Sheets

FOAM PLUG FOR ENGINE COVER FASTENER POCKET

TECHNICAL FIELD

The disclosed inventive concept relates generally to covers for vehicle engines and to a system for attaching the cover to the engine. More particularly, the disclosed inventive concept relates to an engine cover assembly having a mechanical fastener for attaching the cover to the engine and to a foam insert to fill the fastener pocket formed in the cover and to thereby conceal the fastener.

BACKGROUND OF THE INVENTION

The engine compartment of the modern vehicle has an appearance that is quite different from that of its predecessors. For decades following the introduction of the motor vehicle, the engine compartment was generally ignored by designers who, instead, focused on the exterior and interior of the vehicle. The engine compartment of the production vehicle (as opposed to the show vehicle) was left entirely to engineers and thus was solely functional.

Nowadays, however, designers are engaged to improve the overall appearance of the engine compartment. The general result of these efforts is the inclusion in the engine compartment of an engine cover that covers at least some of the vehicle's engine. Known covers have a variety of shapes and styles and vary in the degree to which they cover the engine. The engine cover is typically but not exclusively formed from a polymerized material such as soft polyurethane (PUR) foam.

Known methods for attaching the engine cover to the engine itself include fitting stud bolts to strategic locations on the engine, applying appropriate torque to the stud bolts, installing the engine cover having pockets into which the stud bolts are fitted, and running down attachment nuts to secure the engine cover in position. The pockets are formed in the cover to meet the cover's mating component. The pockets are ordinarily wide enough to meet necessary attachment tooling requirements.

The exposed fasteners, such as the nut and stud bolt combination conventionally used to attach the engine cover to the engine, are traditionally left exposed in their respective pockets. The exposed fasteners do not meet current under-hood appearance requirements. Accordingly, a common challenge for the designer of the modern engine cover is the need to combine functionality and serviceability with aesthetics in the relatively small space typically provided in the modern engine compartment. Consideration must therefore be given to ease of installation to maintain competitive assembly costs and ease of removability of the cover while giving assurance that the engine cover effectively provides good aesthetics. Known solutions to attaching the engine cover fail to provide a solution to the challenge faced by exposed fasteners.

As in so many areas of vehicle technology there is always room for improvement related to the design of engine covers and to their methods of installation. A new approach to attaching an engine cover to an engine while maintaining optimum aesthetic appearance is needed to address the problems associated with known arrangements.

SUMMARY OF THE INVENTION

The disclosed inventive concept provides a convenient, practical and cost-effective solution to the challenge faced by covering mechanical fasteners that hold the engine cover to the engine. The disclosed inventive concept thus provides an ideal solution to the problem of appearance degradation caused by the use of mechanical fasteners.

The arrangement of the disclosed inventive concept includes a concealing plug for use in the pocket of an engine cover to hide the mechanical fastener from view. The concealing plug may be readily installed in the cover pocket and may be easily removed to allow disassembly of the cover fasteners and subsequent removal of the engine cover as needed.

The concealing plug is profiled so as to lockably connect with the wall of the cover pocket. Particularly, the concealing plug includes a conical wall having an upper end and a lower end having a fastener-receiving recessed area. The upper end of the concealing plug has a substantially planar outer surface that is continuous with an upper circumferential ring. A lower circumferential ring is spaced apart from the upper ring. The lower end of the concealing plug includes a recessed area for receiving the upper end of the fastener when the plug is in position in the pocket. The plug may be composed of any of several polymerized materials, such as a polyurethane.

The fastener pocket of the engine cover includes upper and lower grooves having a ring area formed therebetween. When the concealing plug is fitted in the cover pocket, the upper circumferential ring of the plug nests with the upper groove of the pocket, the recessed area of the plug nests with the ring area, and the lower circumferential ring of the plug nests with the lower groove of the pocket, thereby providing a fluid-tight seal. The base of the pocket includes a stud-passing aperture.

A stud-receiving anchor is attached to the engine and a cover-attaching stud is fitted to the anchor. A compression-limiting spacer is placed on the upper surface of the anchor. The engine cover is positioned on the engine such that the cover attaching stud is passed through the stud-passing aperture of the cover. A fastening nut is then threaded onto the cover-attaching stud until it comes into contact with the compression-limiting spacer.

After the fastening nut is fully attached, the concealing plug is inserted without the need for the use of a tool. Removal of the concealing plug can be easily achieved by using a tool for prying the concealing plug out of position, such as by use of a screwdriver or a similar prying tool.

The above advantages and other advantages and features will be readily apparent from the following detailed description of the preferred embodiments when taken in connection with the accompanying drawings.

BRIEF DESCRIPTION OF THE DRAWINGS

For a more complete understanding of this invention, reference should now be made to the embodiments illustrated in greater detail in the accompanying drawings and described below by way of examples of the invention wherein.

DETAILED DESCRIPTION OF THE PREFERRED EMBODIMENT

Figure 1:
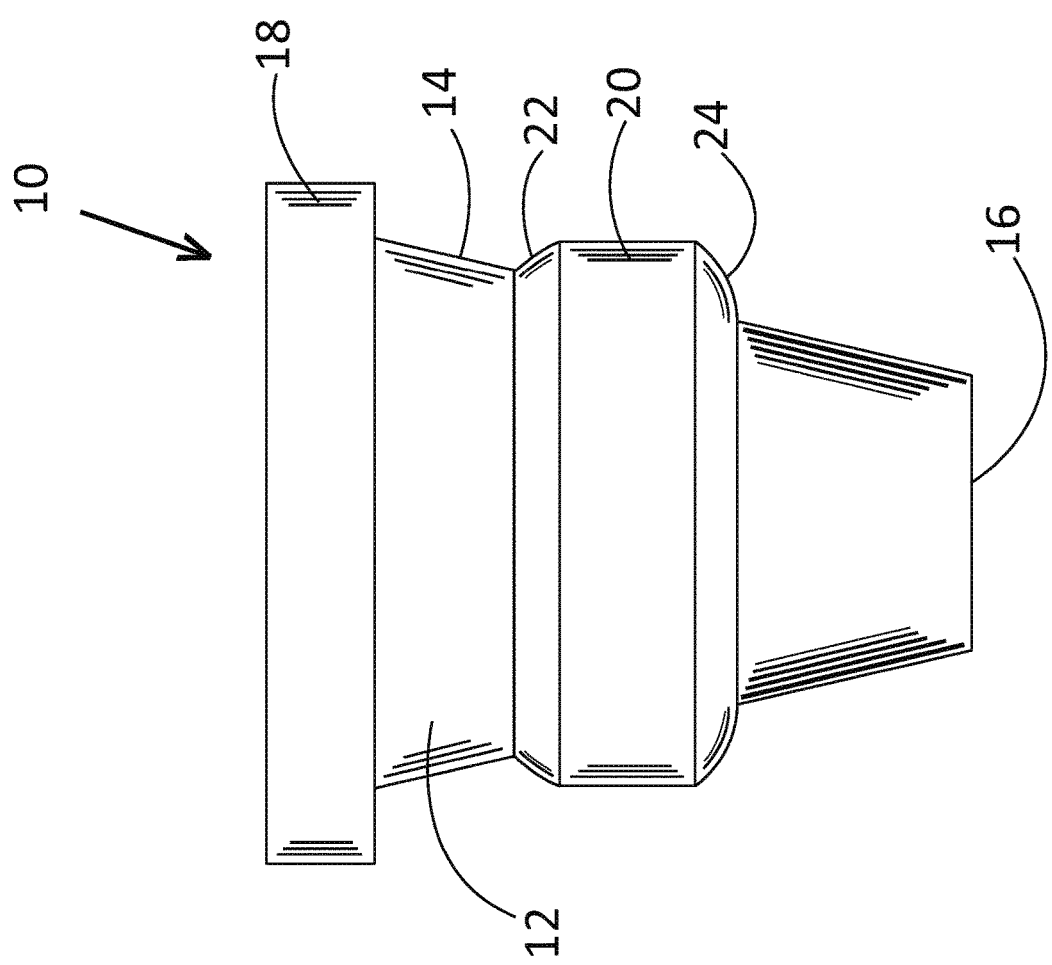
FIG. 1 is a side view of the foam plug for an engine cover according to the disclosed inventive concept.

In the following figures, the same reference numerals will be used to refer to the same components. In the following description, various operating parameters and components are described for different constructed embodiments. These specific parameters and components are included as examples and are not meant to be limiting.

The accompanying figures illustrate an arrangement for providing a finished and clean look to an engine cover for a vehicle. The fastener-concealing foam plug is readily adapted for any fastener pocket, is inexpensive to produce, and may be readily inserted into and removed from the fastener pocket. It is to be understood that the illustrated foam plug as illustrated is not to be restricted to the configuration shown in the figures which is intended as being illustrative without being limiting.

Figure 2:
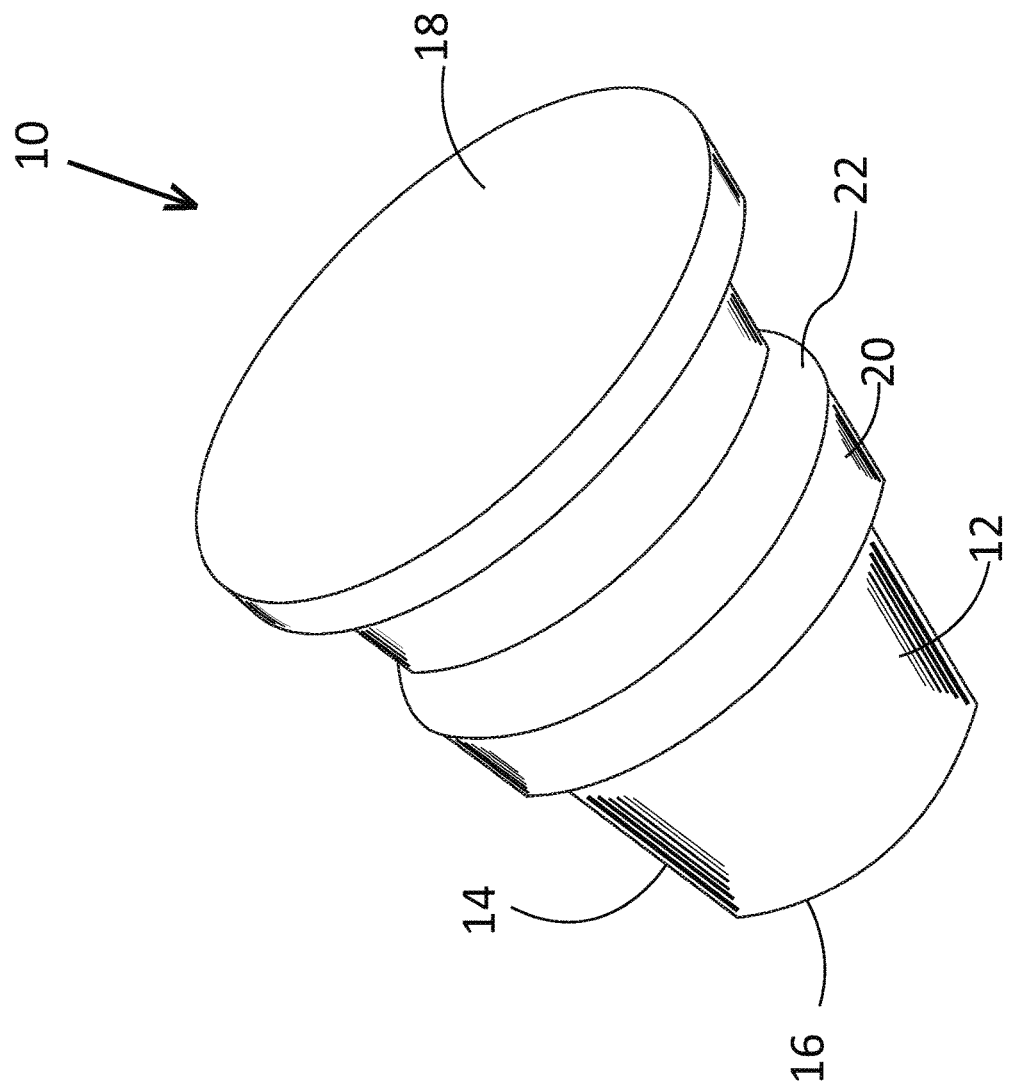
FIG. 2 is a perspective view of the foam plug of FIG. 1.

Referring to FIGS. 1 and 2, a fastener-concealing foam plug, generally illustrated as 10, is shown in isolation. As noted, the illustrated configuration of the foam plug 10 as shown in the figures is only suggestive and is not intended as being limiting. The concealing foam plug 10 may be formed from any of several polymerized materials, including foamed or solid polymers. The concealing foam plug 10 includes a body 12 having a conical sidewall 14. The body 12 further includes a base wall 16 and a top wall 18.

The fastener-concealing foam plug 10 includes a structure for lockably and releasably interconnecting with the interior wall of the engine cover pocket. This structure is a ring 20 having an upper ramped surface 22 and a lower ramped surface 24. The configuration of the ramped surfaces 22 and 24 allow the fastener-concealing foam plug 10 to be readily inserted and removed from the fastener pocket.

Figure 3:
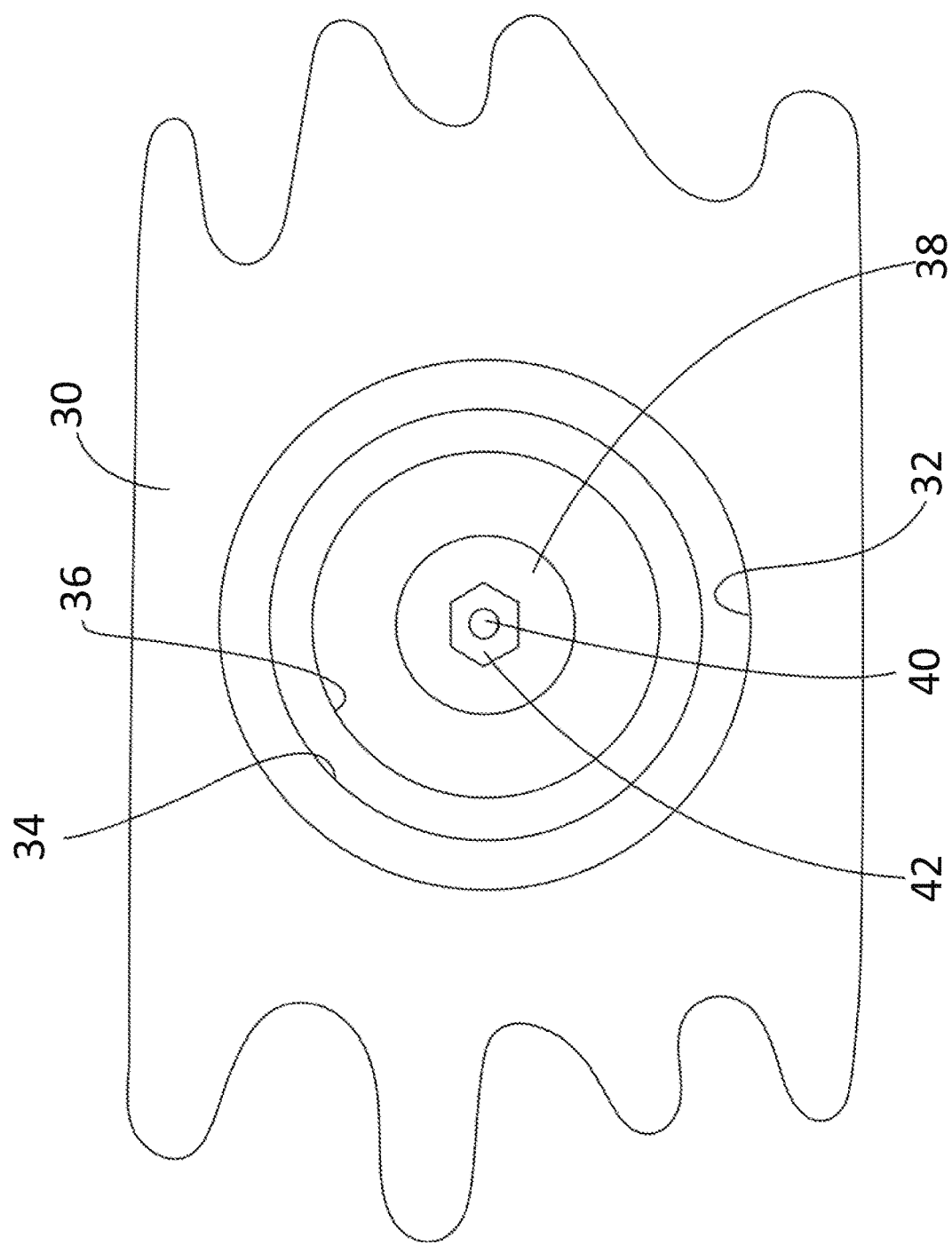
FIG. 3 is a top view of a portion of an engine cover illustrating a fastener pocket formed therein in which a fastener can be seen before insertion of the concealing foam plug of the disclosed inventive concept.

Referring to FIG. 3, a top view of a portion of an engine cover 30 having a fastener pocket 32 is illustrated. As is known, the engine cover 30 may be made from any of several materials including, without limitation, polyurethane. Several fastener pockets 32 may be formed in the engine cover 30 though only a fastener pocket 32 is illustrated for the sake of simplicity.

The fastener pocket 32 includes an upper shoulder 34 and a lower shoulder 36. A base wall 38 is formed at the lower end of the fastener pocket 32. While a variety of methods mechanically fastening the engine cover 30 to the engine may be used, a preferred method is illustrated as including an engine cover stud 40 onto which a fastening nut 42 may be threaded.

Figure 4:
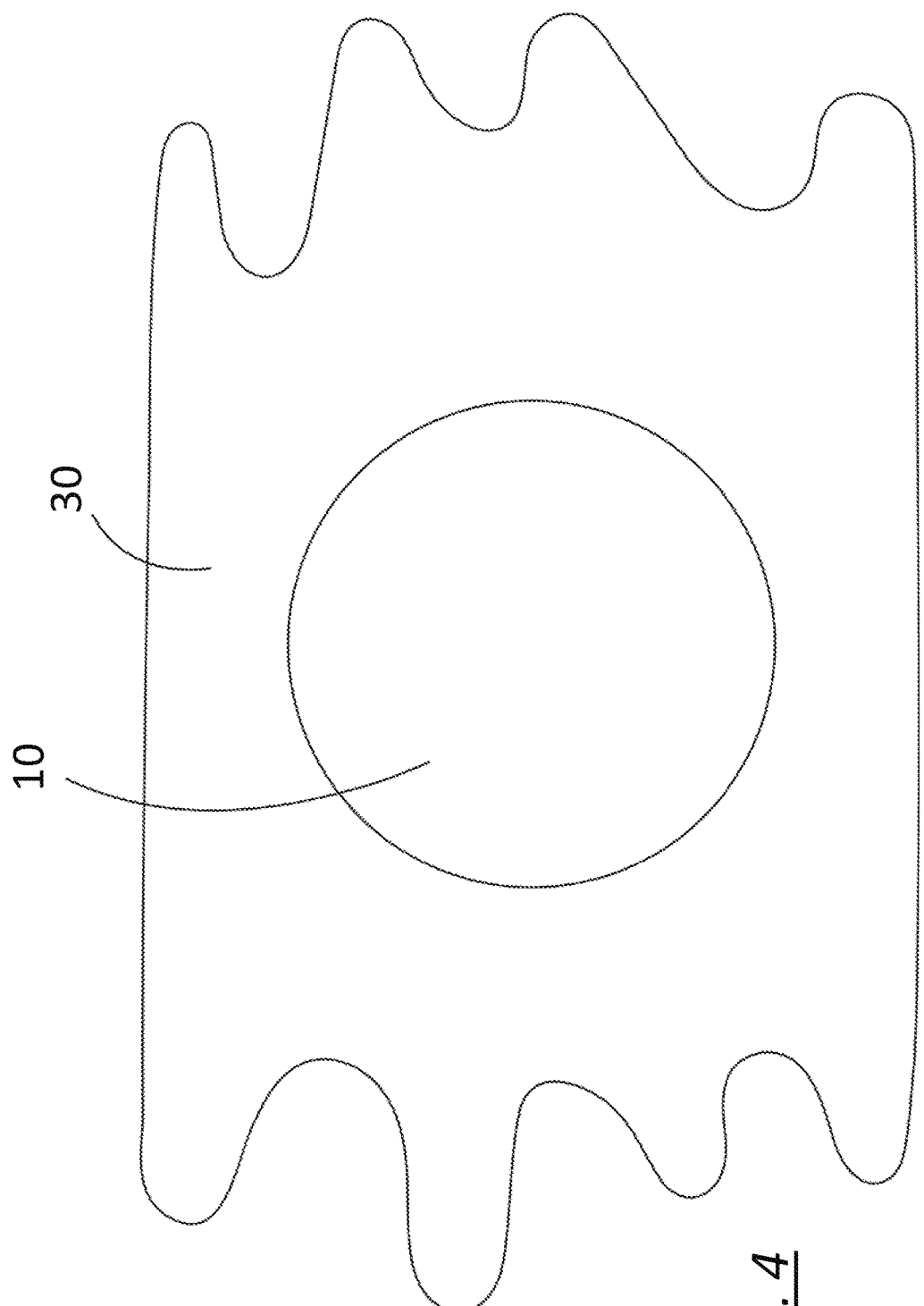
FIG. 4 is the same view of a portion of an engine cover illustrated in FIG. 3 but showing the foam plug of the disclosed inventive concept in place in the fastener pocket.

Referring to FIG. 4, a top view of a portion of the engine cover 30 is also illustrated. However, in this view, the fastener-concealing foam plug 10 has been securely fitted into the fastener pocket 32. As illustrated in FIG. 4, the presence of the fastener-concealing foam plug 10 gives the engine cover 30 a finished and clean look without compromising the removability of the engine cover 30. The fastener-concealing foam plug 10 may be readily installed into the fastener pocket 32 upon vehicle assembly or following engine servicing. When engine service is required, the service technician may easily remove the fastener-concealing foam plug 10 by a simple operation using a basic tool such as a screwdriver or a small pry bar.

Figure 5:
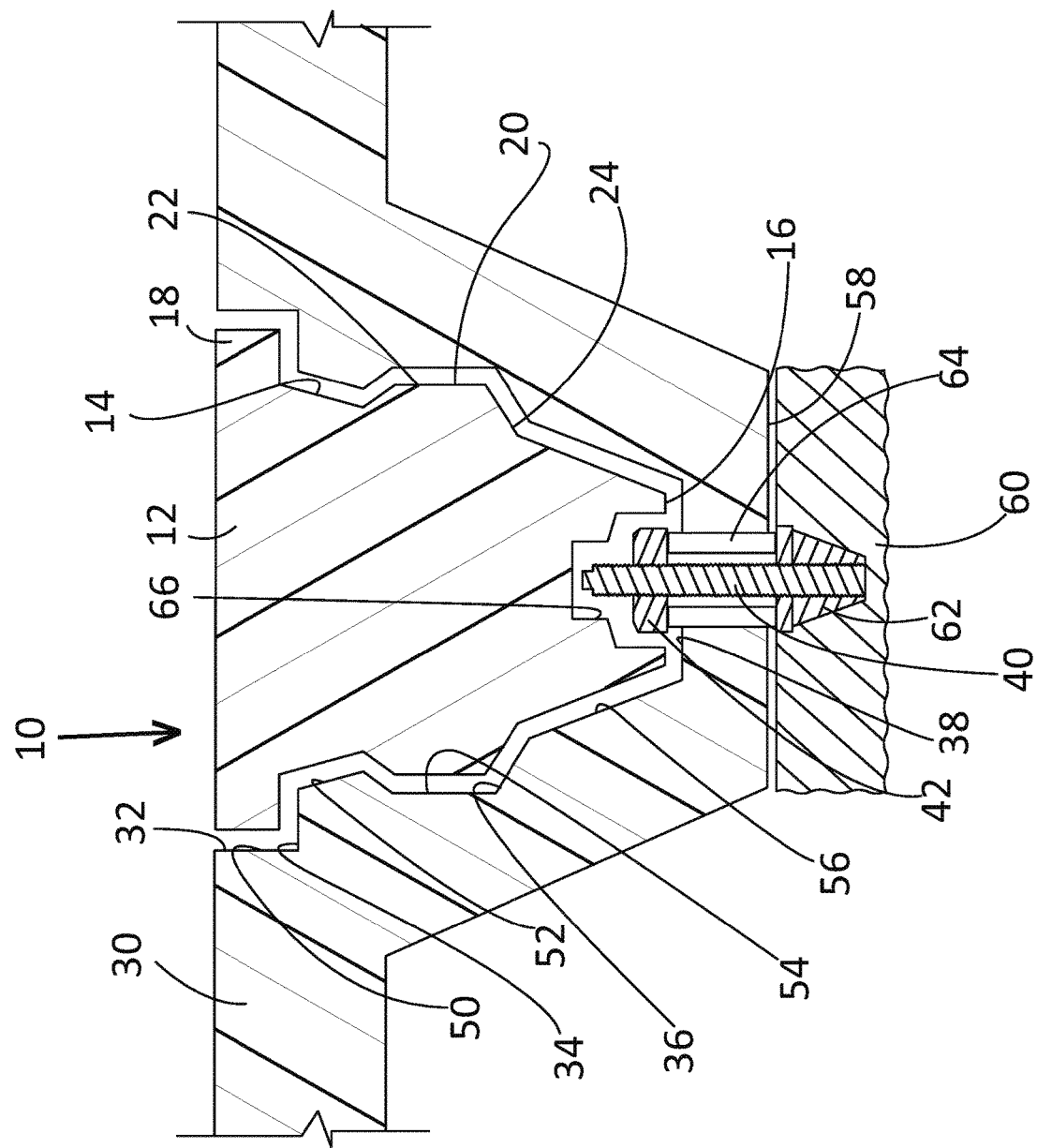
FIG. 5 is a sectional view of a portion of an engine cover and its engine cover pocket, a portion of an engine, the fastener arrangement by which the engine cover is attached to the engine, and the foam plug of the disclosed inventive concept in place in the engine cover pocket to thereby conceal the engine cover fastener.

A sectional view of the fastener-concealing foam plug 10 installed in the fastener pocket 32 and the accompanying fastening hardware is illustrated in FIG. 5. With reference thereto, the fastener pocket 32 includes an upper recess 50 defined by the upper shoulder 34. An inner ring 52 is formed adjacent the upper shoulder 34. A recessed area 54 is formed between the inner ring 52 and the lower shoulder 36. A lower conical wall 56 is formed between the lower shoulder 36 and the base wall 38.

The engine cover 30 includes bottom wall 58 formed on the underside of the fastener pocket 32. When in position, the engine cover 30 is fitted adjacent an engine block 60. A fastener anchor 62 is attached to the engine block 60 into which the engine cover stud 40 is threaded or is otherwise attached. The nut 42 is threaded onto the upper end of the engine cover stud 40. A spacer 64 is fitted between the underside of the nut 42 and the upper side of the fastener anchor 62. The spacer 64 also functions as a load limiter. With the spacer 64 in place, a gap is preferably defined between the engine block 60 and the bottom wall 58 of the cover 30. A recessed area 66 is defined within the central area of the base wall 16. The recessed area 66 provides an open area within which the upper end of the engine cover stud 40 and the nut 42 are positioned when the fastener-concealing foam plug 10 is in position within the fastener pocket 32.

The fastener-concealing foam plug 10 is retained in position within the fastener pocket 32 by the outer side wall profile of the fastener-concealing foam plug 10 which securely engages the inner wall profile of the fastener pocket 32. Particularly, when the fastener-concealing foam plug 10 is in position in the fastener pocket 32, the top wall 18 rests within the upper recess 50 and against the upper shoulder 34, thereby halting further downward movement of the plug 10 upon insertion into the pocket 32 after the plug 10 has reached its maximum insertion depth. At the same time, the ring 20 of the plug 10 engages and rests within the recessed area 54. The conical sidewall 14 of the plug 10 nests against the lower conical wall 56 of the pocket 32 formed between the lower shoulder 36 and the base wall 38.

Because of the elastomeric qualities of the fastener-concealing foam plug 10, when the plug is in position within the pocket 32 it tends to fill the space defined by the pocket 32, thereby maintaining the plug 10 securely within the pocket 32 until a repair technician selects to remove the plug 10 from the pocket 32 for servicing. This same elastomeric quality provides fluid-tight seal that prevents water, oil and debris from accumulating in the pocket 32 and near the fastener assembly. Furthermore, the resilient nature of the plug 10 permits repeated reuse of the plug 10.

One skilled in the art will readily recognize from such discussion, and from the accompanying drawings and claims that various changes, modifications and variations can be made therein without departing from the true spirit and fair scope of the invention as defined by the following claims.

What is claimed is:

1. A removable plug for use with an engine cover having a fastener pocket, the engine cover being attachable to an engine with a fastener, the plug comprising:

an upper end and a lower end, said lower end having a fastener-receiving recessed area;

an upper circumferential ring;

a conical wall formed between said upper circumferential ring and said lower end; and a lower circumferential ring formed on said conical wall thereby dividing said conical wall into an upper conical wall and a lower conical wall, said upper conical wall having a taper and said lower conical wall having a taper, said tapers being the same, said lower circumferential ring having an upper ramped surface immediately adjacent said upper conical wall, a lower ramped surface immediately adjacent said lower conical wall, and a radial surface formed between said upper and lower ramped surfaces.

2. The removable plug of claim 1 wherein said upper end includes an outer top surface, said outer top surface being substantially planar.

3. The removable plug of claim 1 wherein said lower end has an outer surface and said fastening-receiving recessed area is formed in said outer surface.

4. The removable plug of claim 3 wherein said outer surface of said lower end has a center and said fastener-receiving recessed area is formed in said center.

5. The removable plug of claim 1, the plug being formed from a polymerized material.

6. The removable plug of claim 5 wherein said polymerized material is a polyurethane.

7. A removable plug for an engine cover fastener pocket, the cover being attached to the engine by a fastener, the plug comprising:

upper and lower ends, said lower end having a fastener-receiving recessed area;

a conical wall formed between said upper end and said lower end;

a circumferential ring formed on said conical wall defining said upper end; and a retention ring formed on said conical wall between said circumferential ring and said lower end, said retention ring dividing said conical wall into an upper conical wall and a lower conical wall, said upper conical wall and said lower conical wall being collinear.

8. The removable plug for an engine cover of claim 7 wherein said upper end includes an upper surface, said upper surface being substantially planar.

9. The removable plug for an engine cover of claim 8, wherein said circumferential ring is adjacent said outer surface of said upper end, said circumferential ring being continuous with said planar surface.

10. The removable plug for an engine cover of claim 7 wherein said retention ring comprises a first circumferential recessed area, a second circumferential recessed area, and a circumferential ring formed between said first and second recessed areas.

11. The removable plug for an engine cover of claim 10 wherein said first circumferential recessed area is a circumferential groove.

12. The removable plug for an engine cover of claim 10 wherein said first circumferential recessed area is formed adjacent said circumferential ring.

13. The removable plug for an engine cover of claim 7 wherein said lower end has an outer surface and said fastener-receiving area is formed on said outer surface.

14. The removable plug for an engine cover of claim 13 wherein said lower area has a center and said fastener-receiving recessed area is formed in said center.

* * * * *